United States Patent
Golden et al.

(10) Patent No.: US 11,617,870 B2
(45) Date of Patent: Apr. 4, 2023

(54) SYSTEM AND METHOD FOR AUTOMATICALLY ADJUSTING AN EXTERNAL VENTRICULAR DRAIN

(71) Applicant: Lucent Medical Systems, Inc., Kirkland, WA (US)

(72) Inventors: Robert N. Golden, Kirkland, WA (US); Samuel Peter Andreason, Kirkland, WA (US)

(73) Assignee: Lucent Medical Systems, Inc., Kirkland, WA (US)

( * ) Notice: Subject to any disclaimer, the term of this patent is extended or adjusted under 35 U.S.C. 154(b) by 147 days.

(21) Appl. No.: 17/010,661

(22) Filed: Sep. 2, 2020

(65) Prior Publication Data
US 2021/0060315 A1     Mar. 4, 2021

Related U.S. Application Data

(60) Provisional application No. 62/895,440, filed on Sep. 3, 2019.

(51) Int. Cl.
*A61M 27/00*     (2006.01)
*F16M 11/04*     (2006.01)
*F16M 11/18*     (2006.01)

(52) U.S. Cl.
CPC ........ *A61M 27/006* (2013.01); *F16M 11/046* (2013.01); *F16M 11/18* (2013.01);
(Continued)

(58) Field of Classification Search
CPC .......... A61M 27/006; A61M 2027/004; A61M 2205/10; A61M 2205/3344;
(Continued)

(56) References Cited

U.S. PATENT DOCUMENTS 3,957,050 A * 5/1976 Hines, Jr. ............ A61M 27/006
                                                604/326
4,731,056 A * 3/1988 Tremulis ................. A61M 1/70
                                                604/128

(Continued)

FOREIGN PATENT DOCUMENTS

DE         10317308 A1 * 11/2004 .......... A61M 1/0025
WO    WO-2019088902 A1 *  5/2019 ............ A61B 5/021

*Primary Examiner* — Susan S Su
*Assistant Examiner* — Eric Rassavong
(74) *Attorney, Agent, or Firm* — Seed IP Law Group LLP (57) ABSTRACT

A control system and method for automatically adjusting the height of an external ventricular drain from a patient. The height of a pole supporting the bag into which the fluid is drained can be varied, increased or decreased, as driven by a motor. A drip chamber and collection bag that receive the fluid from the patient are attached to the height variable pole. An external fluid pressure tube is coupled to the patient at one end and to a pressure sensor at the other. The pressure sensor is coupled to the height variable pole. The system includes a feedback loop that adjusts the height of the external ventricular drain (EVD) to match the height of the patient's head. As the patient's head moves up or down, the variable height pole moves up and down a corresponding distance to maintain the patient's intracranial or intraspinal pressure, and therefore the cerebrospinal fluid (CSF) drainage rate, at a preset value.

10 Claims, 7 Drawing Sheets

(52) U.S. Cl.
CPC ............... *A61M 2027/004* (2013.01); *A61M 2202/0464* (2013.01); *A61M 2205/10* (2013.01); *A61M 2205/3344* (2013.01); *A61M 2205/7536* (2013.01); *A61M 2209/084* (2013.01)

(58) Field of Classification Search
CPC .... A61M 2205/7536; A61M 2209/084; A61M 1/70; A61M 2210/0693; A61M 2230/62; F16M 11/046; F16M 11/18
See application file for complete search history.

(56) References Cited

U.S. PATENT DOCUMENTS

| | | | | |
|---|---|---|---|---|
| 4,858,619 A * | 8/1989 | Toth | ............... | A61M 27/006 600/561 |
| 4,903,707 A * | 2/1990 | Knute | ............... | A61B 17/3403 600/561 |
| 5,207,661 A * | 5/1993 | Repschlager | ............... | A61M 1/70 604/326 |
| 5,579,774 A * | 12/1996 | Miller | ............... | A61B 5/031 600/487 |
| 5,683,357 A * | 11/1997 | Magram | ............... | A61M 1/70 604/9 |
| 5,772,625 A * | 6/1998 | Krueger | ............... | A61M 1/70 604/9 |
| 5,957,912 A * | 9/1999 | Heitzmann | ............... | A61M 25/0029 604/905 |
| 6,540,727 B2 * | 4/2003 | Harper | ............... | A61M 1/70 604/326 |
| 9,381,331 B2 * | 7/2016 | Seaver | ............... | A61M 27/006 |
| 10,362,947 B2 * | 7/2019 | Mauge | ............... | A61B 5/031 |
| 2001/0011166 A1 * | 8/2001 | Harper | ............... | A61M 1/70 604/322 |
| 2005/0124943 A1 * | 6/2005 | Yang | ............... | A61M 1/0058 604/248 |
| 2009/0054857 A1 * | 2/2009 | Eckermann | ............... | A61M 1/74 604/318 |
| 2011/0257631 A1 * | 10/2011 | Murphy | ............... | G01C 15/004 33/290 |
| 2012/0302938 A1 * | 11/2012 | Browd | ............... | A61M 39/284 604/9 |
| 2014/0276346 A1 * | 9/2014 | Sadanand | ............... | A61B 5/031 604/9 |
| 2016/0331949 A1 * | 11/2016 | Lutz | ............... | A61M 27/006 |
| 2017/0035950 A1 * | 2/2017 | Meyering | ............... | B01D 61/147 |
| 2017/0219450 A1 * | 8/2017 | Swoboda | ............... | A61B 5/02156 |
| 2017/0296796 A1 * | 10/2017 | Pennell | ............... | F16K 15/026 |
| 2018/0055998 A1 * | 3/2018 | Tu | ............... | A61M 27/006 |

\* cited by examiner

SYSTEM AND METHOD FOR AUTOMATICALLY ADJUSTING AN EXTERNAL VENTRICULAR DRAIN

BACKGROUND

Technical Field

The present disclosure is directed to the medical field of neurological treatments for regulating cerebral spinal fluid pressure, and specifically towards maintaining prescribed intracranial or intralumbar CSF pressures via use of an external ventricular drain (EVD) system.

Description of the Related Art

An External Ventricular Drain (EVD) is well-known medical device used to drain excess cerebral spinal fluid (CSF) from a patient's brain or spinal cord. A patient may undergo some trauma, such as injury to the brain, brain stem, or parts of the spinal cord, or suffer an excess of CSF due to a disease process. Often, such injuries or disease cause an excess production, or inadequate drainage of CSF, or leakage of blood or serum into the brain or spinal cord. The excess CSF or other fluid buildup in the brain or spinal cord can cause an increase in the intracranial pressure (ICP), the intraspinal pressure (ISP), or other locations in the CSF connected system. If the pressure becomes too great, this can lead to significant, long-term, patient morbidity and in some cases lead to death.

EVDs typically include a patient drain catheter, a drip chamber, an alignment system, a fluid collecting bag, and associated tubing and valves. The patient drain catheter is inserted through the patient's skull into a brain ventricle, or via the lumbar region of the back into the CSF filled space surrounding the spinal cord. The alignment system is used to calibrate the drip chamber height to the patient's drain location. Current EVDs include a clamp to fasten the EVD system onto a standard intravenous (IV) pole, so that the drip chamber is set at a prescribed height relative to the proximal end of the patient's drain, in order to adjust the pressure at which the CSF flows from the patient into the fluid collecting bag, which also determines the CSF drainage rate.

In current EVD systems, a catheter is connected to the patient's cerebrospinal fluid system in order to remove CSF and other fluids that may be creating excess pressure on the patient's brain. The fluid is drained from the patient at a selected rate. The fluid passes through an external drain tube from the patient's brain or spinal canal to a drip chamber that is positioned above a fluid collection bag. The drip chamber has a fluid drip outlet that is aligned with the inlet of the fluid collection bag. The EVD is adjustably clamped to an IV pole. The external drain tube is connected at a first location on the patient's body, for a ventricular drain usually through the skull above the patient's ear, the back of the skull, or, in some instances, near the patient's temple, and for a lumbar drain through the lower back. Excess fluid is drained from the patient through the drain tube, into the drip chamber, and then into the fluid collection bag.

Notably, the CSF pressure should be maintained within selected limits for the health of the patient. Current EVDs must be manually calibrated and adjusted on a frequent schedule by a nurse or other clinician to account for changes in a patient's head or lumbar height or position, by raising or lowering the clamped position on the IV pole accordingly. If the EVD height is not adjusted after a patient changes position, severe injury or death can result.

In addition, current EVDs use an external pressure sensor, connected via a manual stopcock to the patient's drain line, to periodically measure the patient's ICP or ISP. This is a manual operation requiring first a re-calibration of the EVD height, then rotating the stopcock to connect the pressure sensor to the patient drain while disconnecting the drain from the drip chamber, taking a pressure measurement, rotating the stopcock to disconnect the pressure sensor from the patient drain and reconnecting it to the drip chamber.

Therefore, there is a need in the art for a system and method to automatically adjust the height of EVD systems as a patient moves, and to automatically measure the ICP or ISP.

BRIEF SUMMARY

The present disclosure describes a system and method to automatically adjust, as a patient moves, the relative height between a patient's drain catheter and the EVD, ensuring that excess cerebral spinal fluid is being removed from the patient at the appropriate rate and volume. According to principles of the embodiments as taught here, a system and method is provided to automatically adjust the height of an external ventricular drain (EVD) when a patient's head or lumbar position is raised or lowered relative to the EVD. This will ensure that the patient's intracranial or intraspinal CSF pressure is maintained at the appropriate physician-prescribed pressure, and ensure that the correct CSF drainage rate from the patient to the EVD is maintained.

According to principles taught by present disclosure, a pressure sensing tube is externally coupled to the patient at a sensing location, usually adjacent to the proximal location of the patient's drain tube. The sensing tube is a fluid filled tube that is open to the atmosphere at the patient sensing end and connected to a fluid pressure sensor at the other end. It is important to note that the sensing tube is totally external, and makes no connection to the patient's CSF system. The pressure sensor itself is positioned at a fixed or adjustable location, some distance from the patient, and is removably attached and electrically connected to an electromechanical drive system that can raise and lower a pole to which the EVD drip chamber is clamped.

The pressure sensor measures the fluid column pressure due to the height difference between the external sensing location on the patient and the height of the pressure sensor. By monitoring this pressure, the relative height between the EVD drip chamber and the patient's drain can be determined. The circuitry and drive system then automatically raises or lowers the height of the pole to maintain a fixed height of the EVD drip chamber relative to the patient drain, even as the patient moves.

The fluid in the pressure sensing tube may be water, a saline solution, or any other fluid that maintains a continuous fluid column from the external sensing location to the pressure transducer. The atmospheric pressure end of the tube contains a filter that allows air to communicate with the fluid column, but does not allow fluid in the tube to pass out of the tube.

Then fluid pressure sensor may be of several types, but in some embodiments is an electronic gauge sensor with a resolution of at least 5 mm $H_2O$, and having an electrical output and electrical connection method.

The electromechanical drive system consists of electronic circuitry, a display screen with a user interface, and a motor drive system. The circuitry determines the relative height difference between the patient drain and the drip chamber. The display with user interface allows system settings to be made and pressures and other system values to be displayed. The motor drive system is mechanically connected via a pole to the EVD drip chamber, and raises or lowers the drip chamber to continually maintain the prescribed height difference. The motor drive system may be of several types, including but not limited to an electric motor directly driving connected gears, a linear electric motor, an electric motor driving a hydraulic pump that drives a piston, etc.

The electromechanical drive system is attached to the intravenous pole to which the EVD system itself is clamped. In some embodiments, the electromechanical drive system is incorporated into the intravenous pole itself, raising and lowering a moveable section of the pole to which the EVD is attached. In a second embodiment, the drive system is attached below the EVD system. In a third embodiment, the drive system may be attached above the EVD system.

The electromechanical drive system may also contain circuitry and sensors to monitor the rate and direction of motion of the motor drive system, an encoder means to measure the height of the moveable section of the pole, display means for current and preset pressures and EVD drip chamber height, and alarm means to alert medical personnel if the pressure in the fluid column changes beyond preset limits, or the drive system malfunctions.

The electromechanical drive system and attached pressure sensor may be powered by primary or rechargeable batteries, or by a connection via a power supply to room electricity.

According to one alternative embodiment, it is also possible to automatically measure the pressure of the patient's CSF system. In contrast to the prior art, this can be done without connecting to the EVD fluid drain line itself. In this embodiment, an electronic drip counter is positioned either outside or inside the EVD drip chamber to sense every time a fluid drop falls from the drip chamber into the fluid collection bag. The drip rate is indicative of the pressure difference between the inlet to the drip chamber and the patient's ICP or ISP. The pole supporting the EVD drip chamber is automatically raised until the drip rate falls to a very slow rate. This indicates that the pressure difference is approaching zero. The pole is then slightly raised until the drips have just barely stopped. Preferably the pole is raised to the height at which a drip is suspended from the top of the drip tube, and has not yet fallen but extends out of the drip tube a very slight difference. The height at which the dripping stops, but with a small drop just extending from the end of the tube, is indicative of the patient's actual ICP or ISP.

According to further alternative embodiments, the sensing tube can run to a pressure sensor connected to a patient's bed, the floor, or some location other than the pole itself. The pressure sensor can send, via a wireless transmitter, the sensed measure of the patient's fluid column from the height of the ear to the floor to a received at the drip chamber connection pole. The height of the drip chamber is measure via the linear actuator's drive mechanism encoder. The height of the pole is adjusted accordingly to match the prescribed patient pressure in order to ensure that the drip chamber is at the correct height. This alternative embodiment provides the technological improvement of avoiding a long fluid filled tube from the patient to the drip chamber pole.

According to a further alternative embodiment, one fluid filled sensing tube runs from the patient's drain location to one inlet port of a differential-pressure sensor, and a second fluid filled tube runs from the EVD drip chamber at the height of its outlet orifice (or some other fixed location), to the other inlet port of the pressure sensor. In this embodiment, the pressure sensor is plugged into a stationary interface box at the base of the drip chamber pole and the pole height is adjusted as necessary to maintain the measured differential fluid pressure corresponding to the prescribed patient pressure. The implementation provides the technological improvement of rendering a pole height encoder unnecessary by measuring differential pressure.

DETAILED DESCRIPTION

Figure 1A:
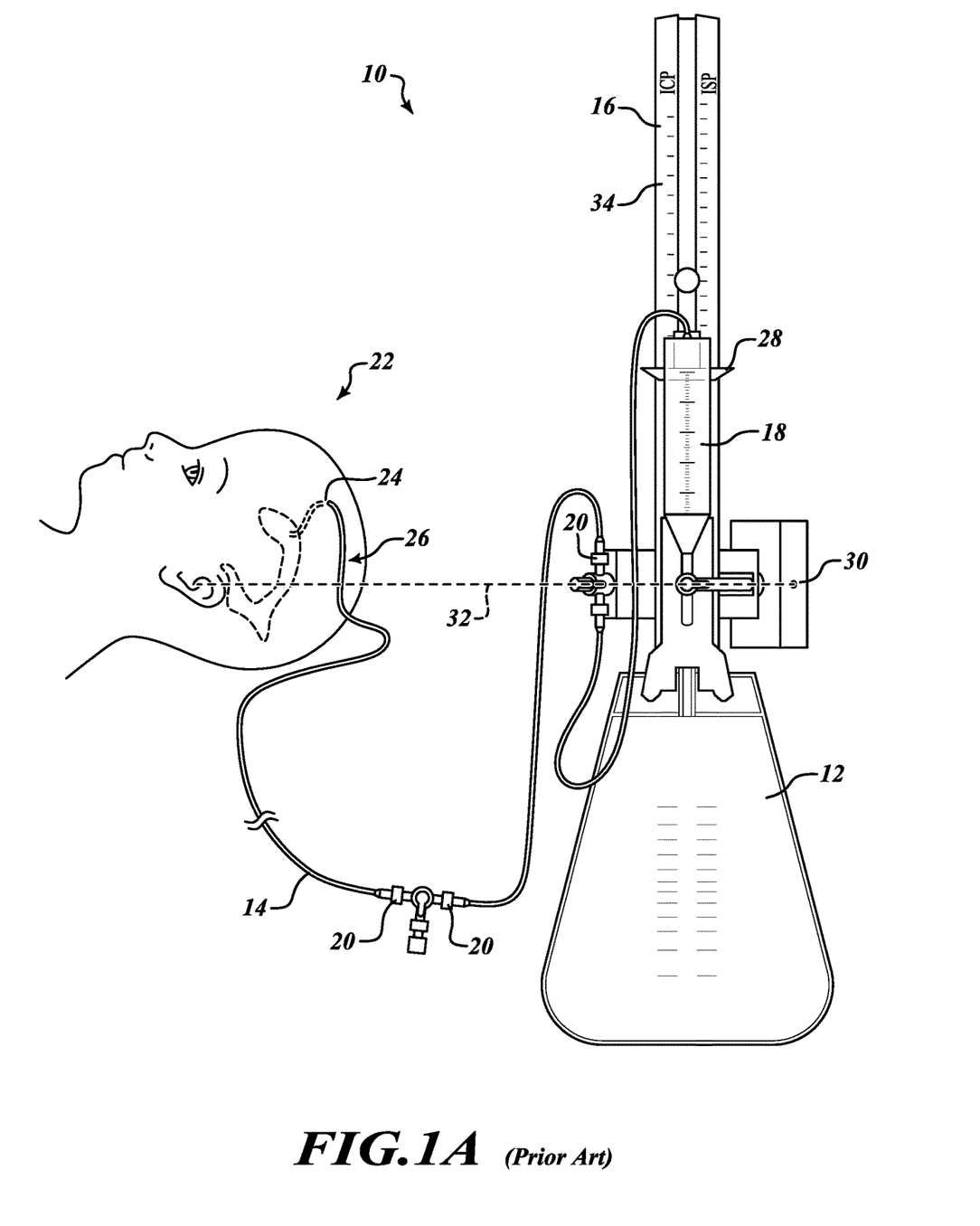
FIG. 1A is a schematic of a prior art External Ventricular Drain system in use on a patient.
Figure 1B:
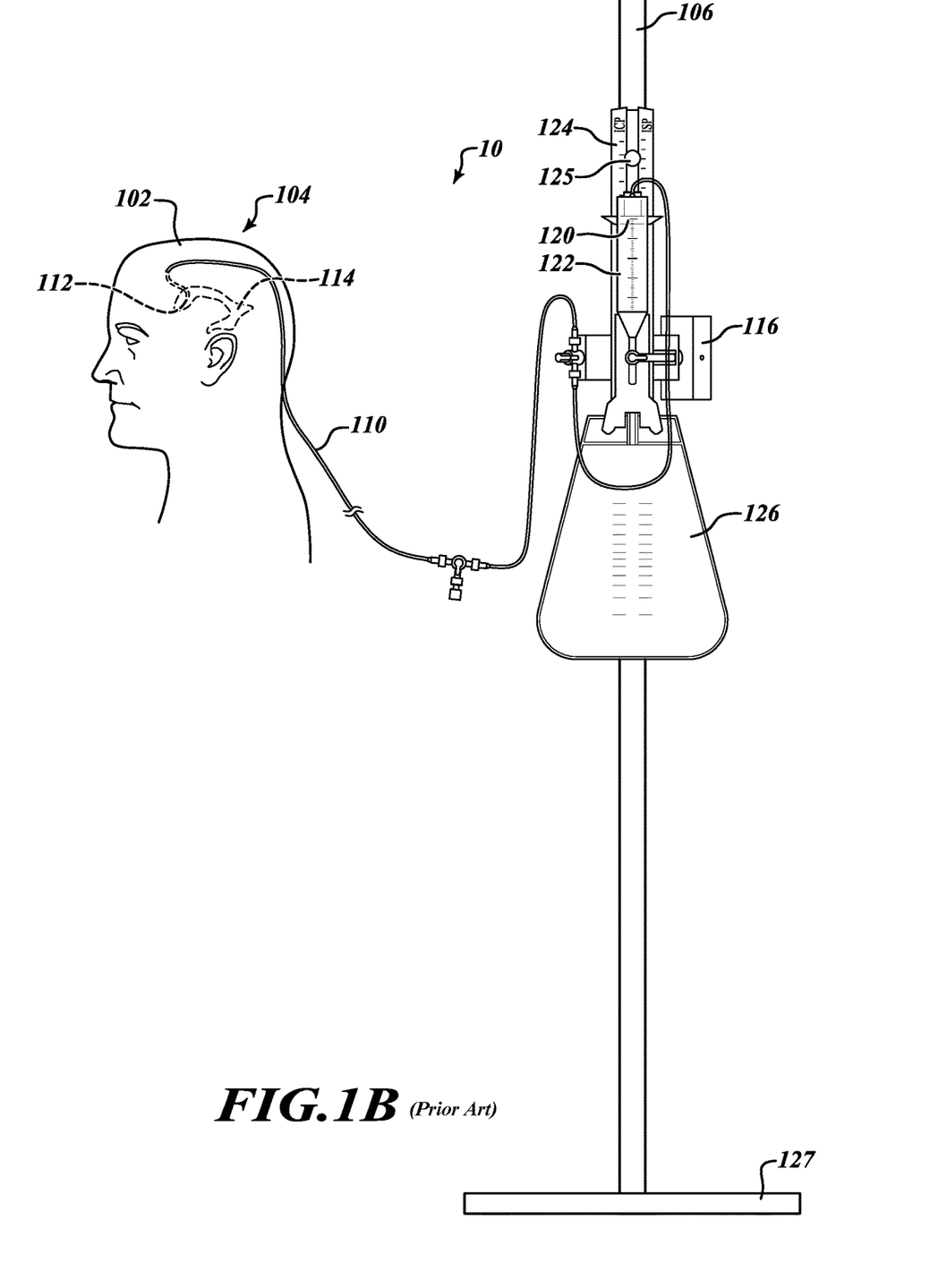
FIG. 1B shows prior art EVD system 1A clamped to a standard IV pole to align the drip chamber height with the height of the proximal end of the patient's drain catheter inside the patient.

FIGS. 1A and 1B illustrate an External Ventricular Drain (EVD) system 10 for collecting excess cerebral spinal fluid from a patient. The EVD system 10 includes a fluid collecting bag 12, a tube 14 that receives fluid from the patient's cerebral system, a drip chamber 18, and a measuring ruler 16. This is a currently available commercial system of the type well known in the art. The EVD system 10 includes one or more valves 20 that are coupled to terminate or start the flow of fluid from a patient. The treatment process in which excess fluid is removed from a patient 22 starts with the connecting of the proximal end, namely the inlet end 24, of the patient drain catheter system 26 being inserted into fluid communication with the cerebral spinal fluid, such as the brain fluid, the brain stem, or the spinal cord. This connection is made using well known techniques for creating a hole into the skull or other location of the patient 22 and creating a fluid-type seal at the inlet end 24 so that the drain catheter system 26 is fluid connected to the cerebral spinal fluid of the patient 22.

The distal end, namely the outlet end of the EVD system 10 is coupled to the drip chamber 18 via tubing 14 and various valves 20. The physician, as part of the medical treatment, will prescribe a patient drain pressure in order to properly remove the excess fluid building up from the injured tissue. Typically, the patient drain pressure is measured in either centimeters of $H_2O$ or mmHg (millimeters of Mercury). Once the proper drain pressure has been prescribed by a physician, this is maintained in the system by setting the relatively height between the inlet end 24 of catheter 26 and the outlet end 28 from which the fluid enters the drip chamber 18. After the target fluid pressure has been prescribed by a physician, the drip chamber 18 is set at a selected height on the measuring ruler 16 to reach the selected pressure. By setting the height of the outlet 28 at the chamber 18 relative to the inlet end 24, the excess pressure that will be drained is established.

To achieve the prescribed value, the EVD is first calibrated to zero pressure by aligning a location on the patient, for example, the lobe of the patient's ear with the drip chamber discharge opening. Current systems have a laser 30 which outputs laser light 32, which is aligned with the bottom of the drip chamber 18 that shines a light at a selected location on the patient. This may be done using a laser, or any other sighting mechanism. The drip chamber 18 is then raised above the zero level to a selected height, according to the prescribed pressure by the physician, which determines the rate at which cerebral spinal fluid is drained from the patient and the target pressure for the fluid to reach. The higher the height of the outlet 28, the slower the drainage and also the higher the pressure in the patient's 22 cerebral spinal fluid pressure. The patient's 22 spinal fluid pressure must overcome the fluid column pressure within the catheter line 14 and the height of the drip tube 14 in order to have the fluid leave the patient 22 and enter the bag 12.

The goal of the prior art EVD system 10 is maintain a safe cerebral spinal fluid pressure. The markings 34 on the measuring device 16 are set at precise values so the exact pressure can be selected to maintain the prescribed pressure inside the patient cerebral fluid.

As shown in FIG. 1B, the prior art system is set based on the patient's head or body being at the same relative location to the EVD system 10. Since the pressure is set between the relative height between the patient 22 and the drip chamber 18, in order to achieve the prescribed pressure, the same relative height difference between the patient 22 and the EVD system 10 must be maintained at all times. According to the current state of the art, after the original EVD calibration and pressure levels are set, the patient is instructed to not move their head up or down in order to ensure that the exact pressure is maintained as prescribed by the physician. Accordingly, the discharge end 28 is set at a certain height above the inlet chamber 24 so that the cerebral spinal fluid pressure must exceed a certain threshold value in order to enter the catheter 14 and be output at the drip chamber 18 and the patient 22 and those taking care of the patient are instructed to not move the patient's head for long periods of time, for example, 12 hours or in some cases 2-4 days.

Unfortunately, in current prior art system, if the patient's head or body is raised or lower, then the initial EVD calibration is no longer valid. Since the fluid flow rate is based on the relative pressure at each end of the tube 14, if the patient 22 changes the height of their head having the inlet 24 relative the height of the outlet 28 as set on the measuring ruler 16, the fluid flow rate will no longer by the amount set by the physician. If patient moves their head down, causing the fluid inlet 24 to be lower than when it was set by the physician, less fluid will drain from the system and the patient 22 will not get the relief they needed. On the other hand, if the patient's head is moved up then more fluid will flow than set by the physician, and, if the inlet 24 becomes higher than the outlet 28 at the top of the drip chamber, then fluid will continue to drain from the patient's brain fluid system until a substantial amount of the fluid is out of the patient 22, which can cause significant harm to the patient.

Using prior art EVDs, if the patient's fluid pressure needs to be monitored, this can only be done with a pressure sensor that is connected to the patient's drain catheter 14. However, the pressure sensor can only make an accurate measurement when the fluid line is closed. Therefore, when the pressure is being sensed directly by the measuring sensor, the valves 20 are shut during which a measurement is taken. Accordingly, this is done only periodically and injury might occur to the patient if the head or body height is changed between measurements, because the drainage rate may become too low or too high.

The system shown in FIGS. 2A-4B illustrates various embodiments for ensuring that the physician-prescribed pressure in the External Ventricular Drain is maintained as disclosed herein. These various embodiments will now be described with respect to these figures. The system of the present disclosure automatically senses and adjusts the relative height between the patient's drain and the height of the EVD drip chamber, to maintain a prescribed ICP or ISP fluid pressure and fluid drain rate, as will now be described.

Figures 2A, 2B:
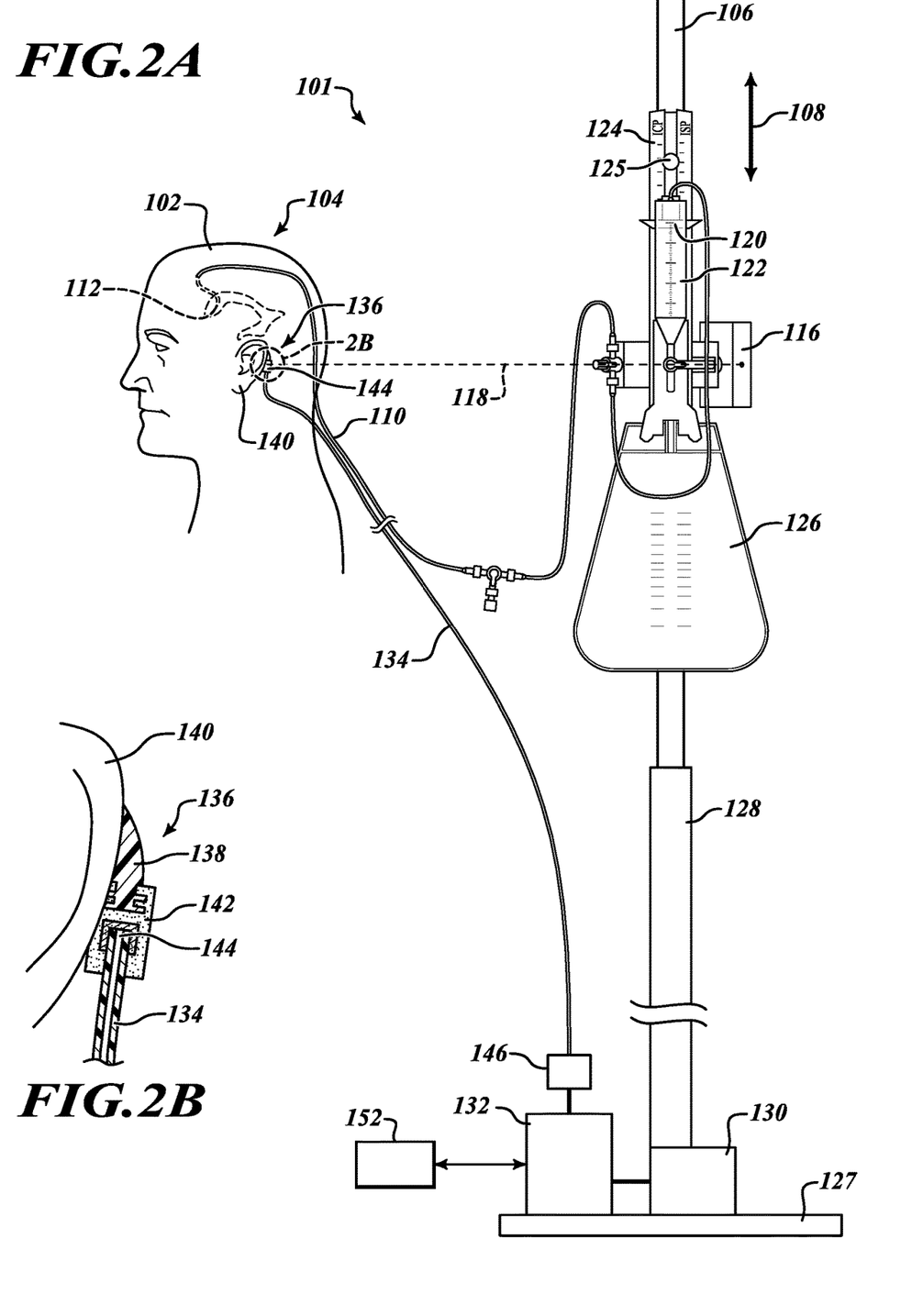
FIG. 2A is an embodiment of an automatic fluid pressure adjustment system according to principles of the present disclosure.
FIG. 2B is a schematic of a filter at a first end of a pressure sensing tube.

According to one or more embodiments as described herein, an automatically adjustable External Ventricular Drain (EVD) system 101 is disclosed which can attach to the patient 104 at the head 102 or other parts of the patient's cerebral spinal fluid. Notably, the External Ventricular Drain (EVD) system 101 may be adjusted remotely and does not require manual interaction such as turning a stopcock or opening/closing a valve. The initial setup of the automatically adjustable External Ventricular Drain (EVD) system 101 as shown in FIG. 2A. In some embodiments, some aspects of the initial setup of the system 101 are similar to that for the prior art shown in FIG. 1 for starting of the fluid flow from the brain fluid system of the patient 104.

In some embodiments, an external ventricular drain tube 110 has an inlet 112 which is coupled to the brain fluid system 114 of the patient 104. As previously described with respect to FIG. 1, a laser 116 outputs a laser light 118 that is aligned with a location on the patient 104, preferably an ear, in order to establish a baseline location of the patient 104 relative to the inlet 120 of the drip chamber 122. The height of the drip chamber 122 is moved up and down along the measuring scale 124 to place the inlet 120 of the drip chamber 122 at the location that will achieve the desired target pressure from the brain fluid system 114 of the patient, and the drip chamber 122 empties into a fluid collection bag 126. The difference between the inlet 120 of the drip chamber and the laser line level 118 is the pressure difference that will be maintain between the cerebrospinal fluid in the patient and the fluid being held in the drip bag 126. The measuring scale 124 will provide an indication of this pressure difference that is to be maintained. By keeping the pressure at the outlet of the system, namely at point 120, a certain level higher than a desired ending pressure of the cerebrospinal fluid in the patient, the system can ensure that excess fluid will not be drained from the patient. The exit fluid pressure will always be held some amount higher than the target final pressure of the patient's cerebrospinal fluid.

In this embodiment, the drip chamber 122 and connected collection bag 126 are clamped to the height adjustable pole 106. The pole 106 is coupled to a support base 127. The pole 106 extends from a casing 128 which has a motor 130 coupled to the base thereof. The motor 130 is any acceptable drive motor, such as a stepper motor or the like, which rotates under the direction of the appropriate controller, such as a microprocessor, microcontroller, or the like. Rotation of the drive motor 130 causes the pole 106 to move either upward or downward as indicated by arrow 108, depending on the rotation direction of the motor 130. The height of the pole 106 is monitored by an encoder incorporated into the drive mechanism and casing 128, and which is connected to a system control unit 132. The motor 130 is driven based on the output from a microcontroller contained within the system control unit 132. In one or more embodiments, the system control unit 132 is also associated with a display 152. In some embodiments, the display 152 is connected to the system control unit 132 via a wired connection. In other embodiments, the display 152 is connected to the system control unit 132 via a wireless connection, thus making it easier for the display 152 to be remote from the system control unit 132. In still other embodiments, the display 152 is an interactive display that can send control signals as well as receive information to be displayed.

In the automatically adjustable External Ventricular Drain (EVD) system 101, an external pressure sensing tube 134 is also coupled to the patient 104. The pressure sensing tube 134 can be coupled at any acceptable location, such as the ear, the back of the head, a band around the head, or other fixed location on the patient 104. In a one or more embodiments (as described in FIG. 2A), the pressure sensing tube 134 has a pressure sensor comparison assembly 136 having a first end 144 coupled to the ear 140 of the patient 104. The tube 134 can be attached by any acceptable method which is fixed and cannot be easily moved, for example, an adhesive 138, a strap or other acceptable attaching mechanism. The pressure sensing tube 134 is filled with a sensing liquid. The sensing liquid can be any acceptable liquid, such as water, a saline solution, or a denser fluid, having a density similar to that of the cerebrospinal fluid. In some embodiments, a higher density working fluid may be used that is higher in density than the cerebrospinal fluid. In these cases, this would have the effect of providing a higher gain pressure in the output of the sensor. The higher gain pressure sensor will provide a more sensitive pressure sensor for more easily fine tuning the desired target pressure to be achieved, but without any electrical sensing or circuits. Namely, the gain in sensitivity will be achieved by the different density in the fluids being compared without the use of electrical circuits or electrical sensing of the actual pressure at either fluid location.

Notably, this pressure sensing tube 134 of the External Ventricular Drain (EVD) system 101 measures the pressure associated with the patient 104 externally, such that this pressure measuring is achieved non-invasively. Additionally, since the pressure sensing tube 134 uses the sensing liquid to obtain the pressure measurement, this pressure measurement is achieved non-electrically. Alternatively, the pressure sensing tube 134 may be a height measuring tube. In these embodiments, measuring the relative heights of the ends of the tube, mediated by a fluid pressure measurement is possible for sensing the pressure. Significantly, the External Ventricular Drain (EVD) system 101 provides the technological improvement of using the external pressure sensing tube 134 to measure the patient's cranial pressure without connection to the patient's drain line, and thus, the patient's cerebrospinal fluid. By not connecting to the patient's cerebrospinal fluid, the pressure measurement technique of the External Ventricular Drain (EVD) system 101 dramatically reduces the chance of introducing infection to the patient since no direct contact in made with the patient's cerebrospinal fluid. Accordingly, the pressure sensing tube 134 of the External Ventricular Drain (EVD) system 101 may be used as a disposable pressure sensor since changing out this component does not risk infection by making direct contact in made with the patient's cerebrospinal fluid.

The pressure sensing tube 134 extends from the patient 104 to a pressure sensor 146 removably attached to the system control unit 132. In one embodiment, the pressure sensor 146 is positioned at the second end of the pressure sensing tube 134 and senses the relative pressure difference between the sensing fluid at a first end 144 and the pressure of the sensing fluid at a second end 148 attached to the pressure sensor, see the embodiment of FIG. 2C, described in more detail elsewhere herein. The pressure sensor 146 outputs a signal proportional to the pressure difference between the two ends. The pressure sensor 146 is removably connected to the system control unit 132, and the signal which is output by the pressure transducer 146 is used by the system control unit 132 in order to change the relative height of the drip chamber 122 to maintain the correct relative pressure of the external ventricular drain tube 110 as cerebrospinal fluid is removed from the patient's brain fluid system.

If the patient 104 raises their head, this will cause the pressure sensor 146 to change its output signal indicating that there is now a greater pressure difference between the first end 144 of the sensing tube 134 and the second end 148. As a result of this change, the pressure sensor 146 will output a signal indicating that the relative pressure is increased. The system control unit 132 then causes the motor 130 to drive the pole 106 higher, in an upward direction, as indicated by arrow 108, so that the relative height of the drip chamber 122 remains unchanged compared to that of the inlet 112 of the ventricular drain tube 110. Similarly, if the patient 104 lowers their head, then the relative pressure difference signal output by pressure sensor 146 will become lower, telling the system control unit 132 to cause the drive motor 130 to reduce the height of the pole 106 so that it will go downward as indicated by the arrow 108, maintaining the exact same relative location between the drip chamber 122 and the inlet 112 of the external ventricular drain tube 110. The system relies on a simple pressure measurement, which is very reliable.

In addition, the present system has the benefit of performing the pressure sensor comparison by relying only on direct fluid pressure difference between that of the patient 104 and the inlet 120 to drip chamber 122. The comparison between the pressure in the patient of their cerebrospinal fluid at the first end 144 of the sensor assembly 136 and the drip inlet point 120 is a direct pressure comparison. It might be considered an analog pressure comparison since there is no use of electrical wiring, circuits or sensing to perform this comparison and provide a pressure difference response. The outlet from sensor assembly 136 is an analog pressure value that provides the results of this comparison as a physical pressure. If the pressure is the same in both systems, the result will be a zero difference in the physical pressure output. Thus errors that might occur in electrical systems for sensing, measuring and providing the comparison result do not occur. The results of the pressure comparison as a pressure value are provided to the pressure sensor 146 that will convert this pressure difference into an electrical signal to drive the height of pole either higher or lower to maintain the correct pressure difference between the patient's cerebrospinal fluid system and the inlet drip point 120.

The pressure sensor 146 can be any of several types, but in some embodiments is a gauge transducer with a resolution of at least 5 mm of $H_2O$ having an electrical output signal compatible with the system control unit 132. In some embodiments, the pressure sensor 146 has an output connector that removably plugs into the system control unit 132. The system control unit 132 may include circuitry to monitor the rate and direction of the motor drive system 130, for displaying the current sensor pressure 146, as well as the height of the pole 106, and the attached drip chamber 122. It may also include an alarm that alerts medical personnel if the sensor pressure is above or below a preset limit. In particular, the pressure sensor 146 senses the relative pressure between the two ends of the pressure sensing tube 134. If the relative pressure goes below a selected value, for example because the patient's head is too low, then an alarm may sound. Similarly, if the pressure goes above a selected value, because the patient's head is too high, then an alarm may also sound. The selected thresholds are based upon the movement range of the pole 106. In particular, if the head of the patient 104 goes higher than the permissible movement of the pole 106 resulting in the chamber 122 not being able to rise sufficiently high to maintain the same relative pressure within the drain tube 110, then an alarm will be generated, either by a sound, flashing light, sending a signal to the nurse's station, or similar method. This will alert medical personnel that the patient has moved to a location which is beyond the safe operation of the EVD drain system 101. Since having the head 102 of the patient 104 higher than the drip chamber 122 is the most dangerous medical condition, an alarm will be set at a relatively low threshold value above the safe operating zone of the system resulting in an alarm sounding if the relative pressure between the two ends of the sensing tube 134 becomes greater than the threshold value. Similarly, an alarm can be set at a different threshold value if the pressure becomes too low between the two ends of the sensing tube 134.

While only a single one measurement tube 134 and sensor comparison assembly 136 is shown and described, it is contemplated that two or more such sensors could be used, for example, one for each ear. Thus, two or more measurement tubes 134 may be utilized, for example, one each ear of the patient. This would permit the value of the two pressure differences to be compared and the lower one could be used, for example, if the patient rotated their head 90 degrees from that shown, or a combination of the two values could be used to generate the signal that will vary the height of the pole 106.

In some embodiments of the External Ventricular Drain (EVD) system 101, a filter 142 is positioned on the end of the tube 134 which permits ambient air pressure to be applied to the sensing liquid that is within the pressure sensing tube 134. The filter 142 is of a type that permits ambient air pressure to be applied to an end 144 of the tube 134, but which does not permit fluid filling the tube 134 to exit from the tube.

Figure 2C:
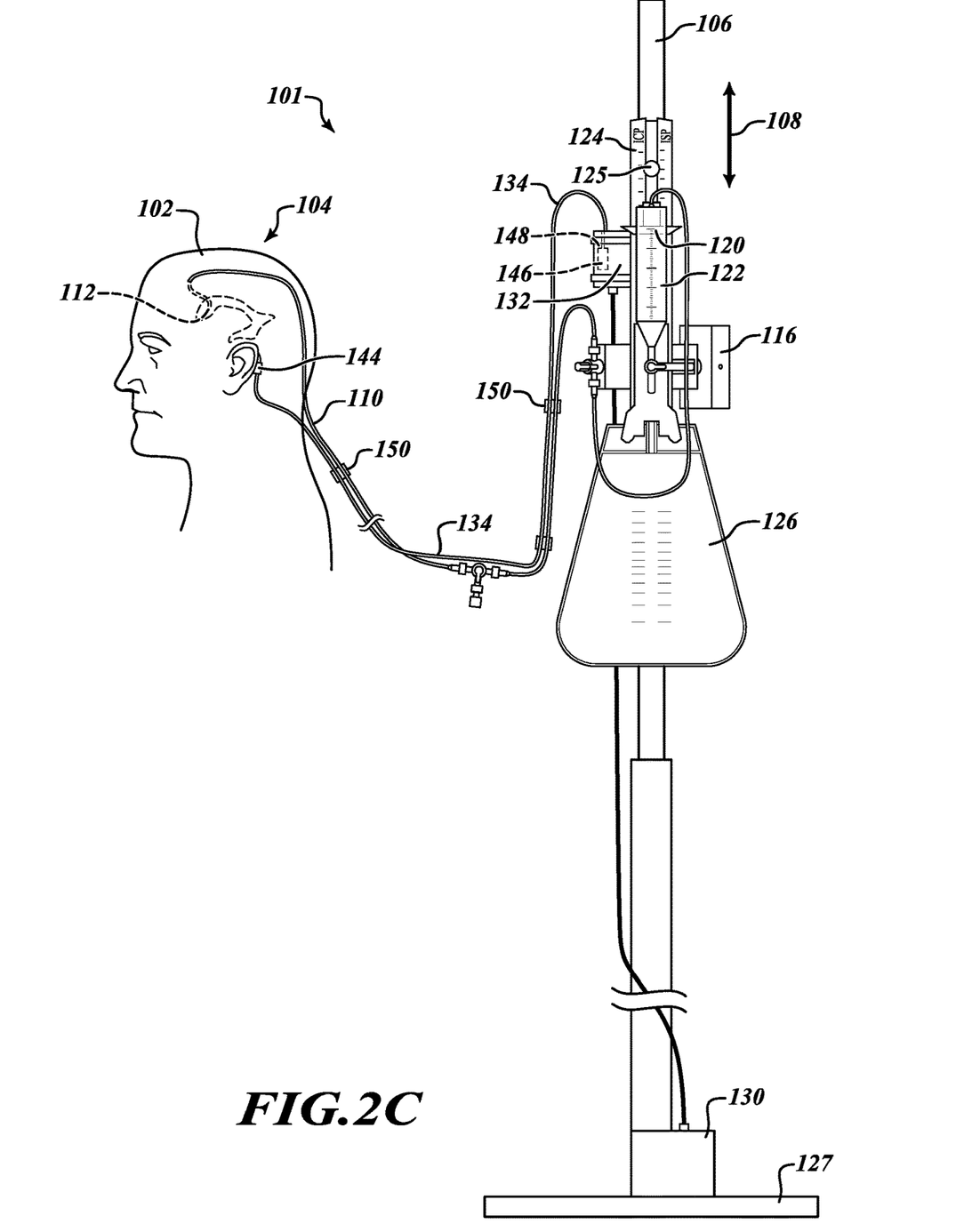
FIG. 2C is also embodiment of an automatic fluid pressure adjustment system according to principles of the present disclosure.

Referring now to FIG. 2C, in another embodiment of the automatically adjustable External Ventricular Drain (EVD) system 101, the pressure sensor 146 includes a microprocessor as well as other signal conditioning features in order to output the proper signal from the control system 130. The electromechanical drive system 130 may include electronic circuitry and a motor drive system. This circuitry determines the difference between the current pressure, as measured by the pressure sensor 146, and the preset pressure value which has been set by the physician. Therefore, this raises and lowers the drip chamber 122 by raising and lowering the pole 106 in order to maintain a constant pressure difference between the inlet 112 on the patient's brain fluid system and the drip chamber 122. The electromechanical drive system 130 can be removably attached to the same pole 106 to which the entire EVD system itself is attached. In one such embodiment, shown in FIG. 2C, the control system 130 is connected to the fixed casing 128 of the pole 106 and it remains completely stationary at all times. In this embodiment, the pole 106 moves up and down, but the casing 128 remains stationary and the control system 130 remains stationary, fixedly attached to the pole 106.

FIG. 2C illustrates an embodiment of the automatically adjustable external ventricular drain system 101. This alternative embodiment of the system 101 is similar to the system described in FIG. 2A and, therefore, common features will not be repeated. There are a few differences which will be highlight in the description that follows. In the initial setup of the pressure sensing system having the sensing tube 134 with the first end 144 coupled to the patient 104 and the other end 148 coupled to the pressure transducer 134, a selected pressure is established relative to the pressure difference between the two ends of the drain tube 110, namely ends 112 and the inlet 120 into the drip chamber 122. When the physician sets the prescribed pressure by moving the drip chamber 122 to the desired location on the measuring gauge 124, he makes an indication that the system is at the desired pressure, such as by pressing a button, inputting a confirmed setting, or other technique. The system, then, will automatically accept the then current pressure difference between the two ends of the tube 134 as the desired pressure difference to maintain at all times. Accordingly, if the patient 104 moves their head upward, the pressure sensor 146 will sense immediately a change in the pressure difference between end 144 and end 148 and will output a signal to move the pole 106 higher. It will move higher an amount equal to that which is needed to match the head 102 of the patient 104. If the patient 104 moves their head down, then a pressure difference between the two ends of the pressure sensing tube 134 and it will, therefore, output a signal to the drive mechanism 130 to move the pole 106 downward to maintain the pressure difference between the two ends at the exact value that existed at the time the physician indicated the pressure was correct based on the location of the drip chamber 122.

The embodiment of FIG. 2C has a further benefit which can be used in the embodiment of FIG. 2A or other embodiments. This additional feature is the use of clasps 150 which couple the ventricular drain line 110 to pressure sensing line 134. Any appropriate clasp may be used for the connector 150, such as a clip, a tube connector, an adhesive, tape, or any acceptable connector which does not impact the fluid pressure or the movement of fluid within the tubes 110 and 134. The clips 150 have the benefit of holding the two tubes 110 and 134 in close proximity to each other for safety, convenience, and simplicity of operation. It is desired to ensure that the sensing tube 134 is not bumped by medical personnel, since it may be pulled out of either end. Normally, the ventricular drain tube 110 is placed in a particularly guarded location to ensure it cannot be bumped, tripped, or otherwise removed by medical personnel by accident. Since the drain tube 110 is the tube providing the medical treatment, special care is taken to ensure that it is not accidentally removed, bumped, or compromised. By using connectors 150 to couple the pressure sensing tube 134 to the ventricular drain tube 110, this reduces the likelihood that the pressure sensing tube 134 will be bumped or accidentally moved and it also increases the visibility of the two tubes to keep them working as a team. The connectors 150 can be used to some extent on the embodiment of FIG. 2A; however, they are most conveniently used on the embodiment of FIG. 2C since the pressure sensor 146 will be moving up and down exactly with the chamber 122 and, therefore, the two tubes 134 and 110 can remain connected for a wide range of operations.

Figure 3:
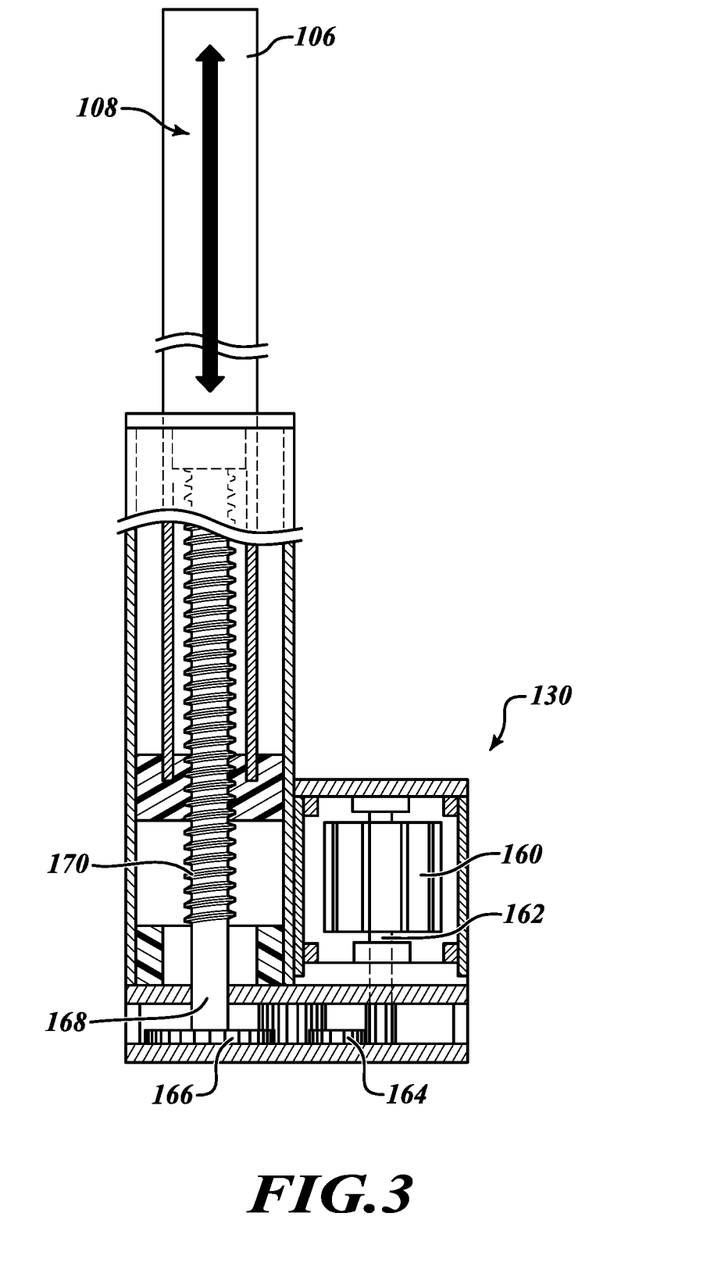
FIG. 3 illustrates a motor drive system for raising and lowering a shaft of a pole according to principles of the present disclosure.

FIG. 3 illustrates one embodiment for the mechanical drive system 130. In this embodiment, a motor 160 has a shaft 162 extending out the bottom thereof and into a gear system 164. The gear system drives a gear 166 coupled to the rotatable shaft 168 which has inclined thread screws 170 mounted thereon. Inside the moveable pole 106 is a mating incline through screw thread for the incline through screw threads 170 causing it to move up or down as the shaft 168 rotates. This is just one example of an acceptable electromechanical drive system and any of a number of other acceptable systems may be used.

Figure 4A:
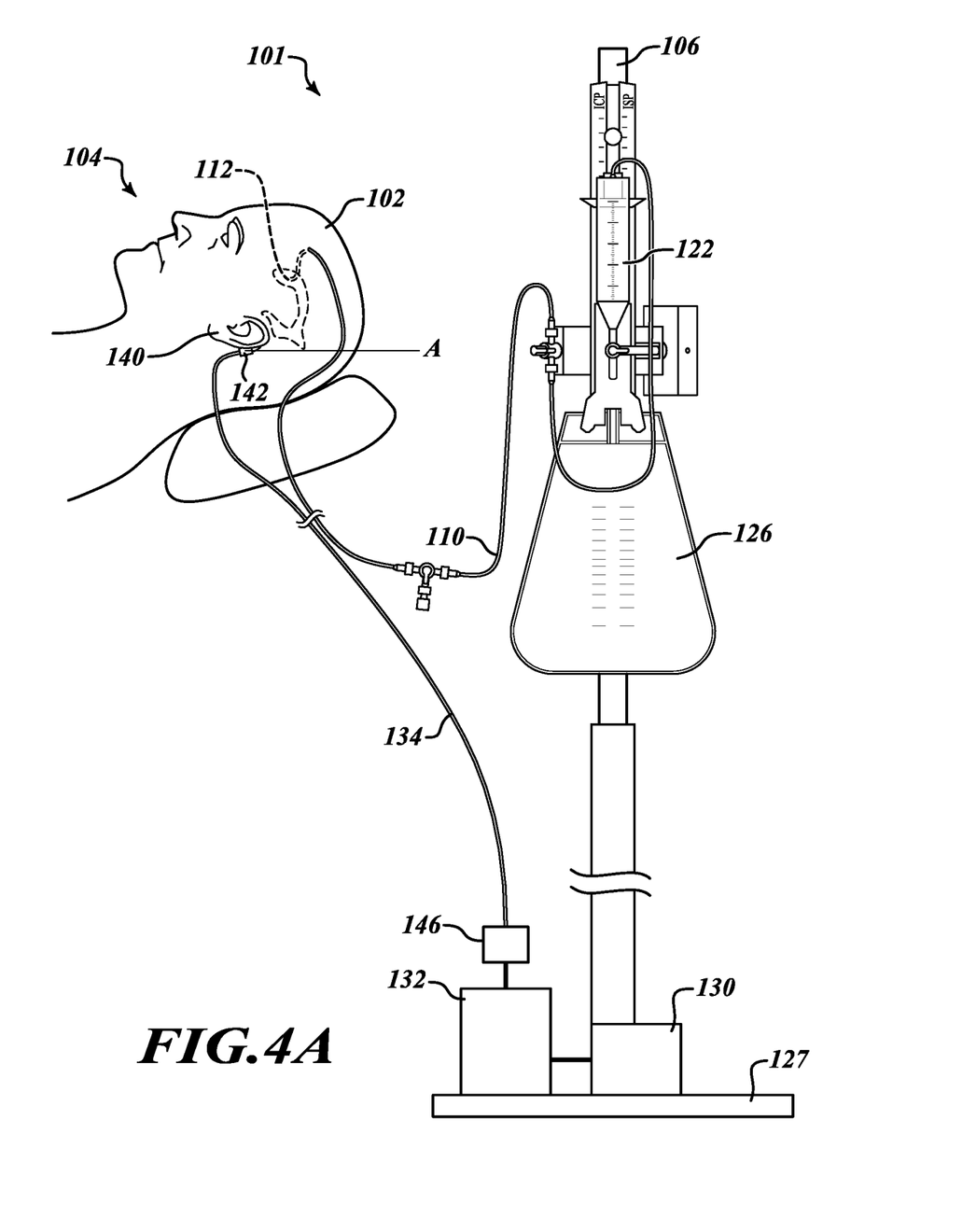
FIGS. 4A and 4B illustrate the automatic height adjustment of the fluid collection system based on the patient moving their head to a different height.
Figure 4B:
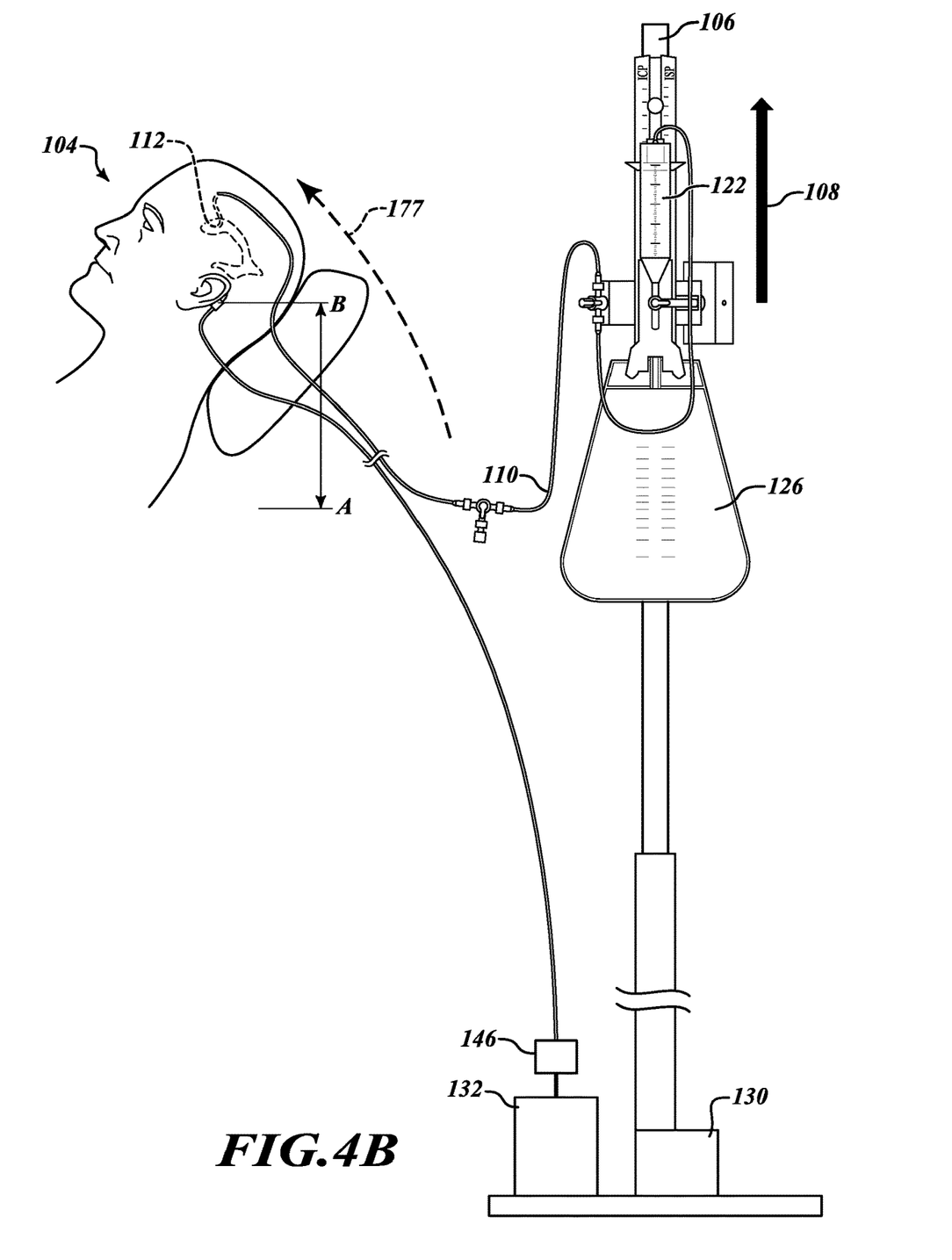

FIGS. 4A and 4B illustrate operation of the embodiment of FIG. 2A, as will now be described. The system is set up as previously described with respect to FIG. 2A in which the patient 104 has an external ventricular drain tube 110 positioned having a first end 112 connected to the brain fluid system and a second connected to the drip chamber 122. A pressure sensing tube 134 is connected to the patient's ear 140 in the manner previously described with respect to FIG. 2B having a filter 142 on the end thereof which permits ambient air pressure to be applied to a sensing fluid inside the tube 134. The patient 104 is reclining, having their head 102 resting so that the first end of the sensing tube 134 is at height A.

FIG. 4B illustrates what happens when the patient 104 raises their head to a new height B. In particular, the patient 104 may have their head raised because the hospital bed is raised up or they move to a new location from height A to height B, as illustrated by dashed line 177. As the patient is moved to be in a more upright position, the first end 144 of the pressure sensing tube 134 goes to a new height B. This change in height is recognized as a change in pressure by the pressure sensor 146. In this embodiment, since it is desired to maintain the pressure at the same, preset value when the system was calibrated, the pole 106 is driven upward by the electromechanical system 130 to a new height. The increased height is equal to the change in height from height A to height B to maintain the relative pressure difference the same between both ends of the pressure sensing tube 134 and, therefore, maintain the relative pressure difference between the first end 112 of the ventricular drain tube 110 and the second end which is connected to the drip chamber 122. As can be seen in FIG. 4B, the pole 106 has risen a height corresponding to the height from A to B.

A system has been described which ensures that the pressure to be relieved from the brain fluid system of the patient 104 that has been prescribed by the physician remains the same, even as the patient changes the height of their head. This will ensure that the system will continue to operate properly and relieve the pressure in the brain fluid system to achieve the correct pressure.

As part of patient treatment with an EVD, the patient's intracranial fluid pressure (ICP) or intraspinal fluid pressure (ISP) is typically measured on a periodic schedule. The present embodiments permit a simple technique to achieve this automatically with the addition of a drip sensor to monitor the drops from the output orifice 120 of the EVD's drip chamber 122. This drip sensor is connected to the system control unit 132, and is capable of measuring the rate at which fluid drops fall from the output orifice 120. If drops are falling, then this indicates that the pressure in the brain fluid system of the patient 104 is greater than the pressure height at which the drip chamber 122 is set on the measuring gauge 124.

If the height of the drip chamber is raised to a position where the fluid drops just stop falling, as monitored by the drip sensor, then the pressure at the drip chamber output orifice will be equal to the ICP or ISP. By automatically raising the drip chamber height to that point, the ICP or ISP can then be determined, displayed, and recorded, because the present embodiments monitor the height of the pole 106, and therefore the height of the attached drip chamber. Methods to estimate the ICP or ISP by monitoring drip rates, are described as follows.

According to one embodiment, it is desirable to make an estimate of when the drips will stop by measuring the drip rate at multiple different drip chamber heights. According to this embodiment, a first measurement of the drip rate is made at a first height location and then the drip chamber 122 is moved to a new height, and the measurement of the drip rate is made at the new location. By making multiple measurements at a plurality of different locations on the measurement gauge 124, an estimate can be made of the patient's ICP or ISP.

According to another embodiment, measurements can be made waiting for two drips to come into the drip chamber and measuring the period between the two drips. After this time period is measured, then the pole can be raised a selected distance. At the new height, the period of time between the two drips is measured again. This can continue for a number of different measurements, or until the period between the two drips becomes too long. The time period between the two drops can be used to project at what height the dripping will stop.

Yet another technique is to move the drip chamber 122 slowly upward until it reaches a location at which a drip is just barely formed exiting from the end of the drain tube 110, but which does not fall out. When the location is reached at which a drip has begun to form, but does not increase in size, nor decrease in size, but remains exactly the same size, projecting slightly from the end 120 of the drain tube 110, but not dropping into the drip chamber 122, then this can be determined to be the correct height which corresponds to the ICP or ISP of the patient 104.

Additional embodiments may also be added to those which have been described herein. According to a first embodiment, a wireless pressure sensor is used in combination with the pressure sensing tube. In this alternative embodiment, the pressure sensing tube 134 is coupled to a single port pressure sensor that is positioned or attached to the patient's bed, the floor, or some fixed location. A wireless transmitter, which may be battery powered or otherwise, will sense the patient's fluid column height using the pressure sensor fluid and transmit this to a receiver in the system control unit 132. One benefit of this embodiment is that it will avoid the use of a long fluid pressure sensing tube 134 that may extend from the patient's head 102 to the system control unit 132.

Yet another alternative embodiment is the use of a dual port differential pressure sensor which has two pressure sensing tubes. According to this alternative embodiment, a first fluid filled pressure sensing tube extends from the patient's ear in the manner described with respect to FIG. 2A to one of the inlet ports of a differential pressure sensor. A second fluid filled tube extends from the drip chamber 122 at the height of its outlet orifice, or some other fixed location, to second inlet port of the differential pressure sensor. In this embodiment, the differential pressure sensor removably connects to the system control unit 132.

The pole height is then adjusted to maintain the measured differential fluid pressure corresponding to the prescribed patient pressure. A technological improvement provided by this embodiment is that the system can maintain a prescribed patient pressure without relying on the use of the motor drive encoder to monitor the pole height.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
    a support base;
    a pole extending from the support base;
    a drip chamber coupled to the pole;
    an external ventricular drain tube having a first end thereof coupled to a patient's cerebrospinal fluid at a first location and being closed off from ambient atmospheric pressure at the first end thereof at the first location and having a second end spaced from the first end, the second end being coupled to the drip chamber;
    a fluid filled pressure sensing tube having a first end thereof coupled to a patient's body at a sensing location that is spaced from the first location and a second end thereof coupled to the pole, the sensing location on the patient's body being at selected location relative to the first location, the pressure sensing tube having a pressure sensing liquid within the pressure sensing tube, the fluid filled pressure sensing tube being open to ambient atmospheric pressure at a first end thereof coupled and receiving the ambient atmospheric pressure at the first end;
    a single pressure sensor at the second end of the pressure sensing tube that senses a relative pressure difference between the ambient atmospheric pressure on the sensing fluid at the first end of the pressure sensing tube and the pressure of the sensing fluid at the second end of the pressure sensing tube and outputs a relative pressure difference signal, the system having only a single pressure sensor;
    a microcontroller that receives the relative pressure difference signal and outputs a drive signal generated from the relative pressure difference signal and having a value selected to maintain the patients cerebrospinal fluid pressure below a first selected threshold value and above a second, selected threshold value;
    a drive motor coupled to the support base, the drive motor receiving the drive signal from the microcontroller; and
    a variable height shaft in the pole coupled to the drive motor that is driven to a selected height based on the drive signal that is generated from the relative pressure difference signal.

2. The system of claim 1 wherein the height of the shaft is raised or lowered to maintain the same relative pressure between first and second ends of an external ventricular drain tube.

3. The system of claim 1 wherein the height of the shaft is raised or lowered to maintain a same relative pressure between the first and second ends of the pressure sensing tube, a height of the second end of the pressure sensing tube being variable based on the value of the drive signal.

4. The system of claim 1 wherein the second end of the pressure sensing tube is coupled to a stationary location on the pole.

5. The system of claim 1 wherein the second end of the pressure sensing tube is coupled to a movable location on the pole that moves up and down as the height of the pole changes.

6. The system of claim 1, further comprising: a filter coupled at the first end of the pressure sensing tube, the filter permitting ambient air pressure to be applied to the sensing liquid at the first end of the tube and prohibiting the sensing liquid from escaping from the first end of the tube.

7. The system of claim 1 wherein the drip chamber and the second end of the external ventricular drain tube coupled to the drip chamber are open to the ambient atmospheric pressure.

8. A method to adjust a height of a drip chamber coupled to an external ventricular drain tube of a patient the method comprising:
    coupling a first end of the external ventricular drain tube to the cerebrospinal fluid of the patient at a first location, the first end being exposed to the pressure for the cerebrospinal fluid and blocked from exposure to ambient atmospheric pressure;
    coupling the drip chamber to a pole;
    coupling a second end of the external ventricular drain tube to the drip chamber, the second being exposed to ambient atmospheric pressure;
    coupling a first end of a pressure sensing tube to a head of the patient at a selected location spaced from the first location;
    maintaining the first end of the pressure sensing open to the ambient atmospheric pressure;
    coupling a second end of the pressure sensing tube to a single pressure sensor;
    outputting a signal from the single pressure sensor to a drive system that includes a microcontroller and mechanical drive components;
    generating by use of the single pressure sensor a relative pressure difference signal and having a value selected to maintain the patients cerebrospinal fluid pressure below a first selected threshold value and above a second, selected threshold value;
    raising or lowering the pole to maintain a pressure of the patient's cerebrospinal fluid below a first selected threshold value and above a second selected threshold value based on the value of the relative pressure difference signal from the single pressure sensor.

9. The method of claim 8 further including:
    coupling the second end of the pressure sensing tube to a stationary location on the pole.

10. The method of claim 8 further including:
    coupling the second end of the pressure sensing tube to a movable location on the pole that moves up and down as the height of the pole changes.

* * * * *